United States Patent [19]

Roberts et al.

[11] Patent Number: 6,058,590
[45] Date of Patent: May 9, 2000

[54] APPARATUS AND METHODS FOR EMBEDDING A BIOCOMPATIBLE MATERIAL IN A POLYMER BONE IMPLANT

[75] Inventors: Jack C. Roberts; Paul J. Biermann; Amy A. Corvelli, all of Columbia, Md.

[73] Assignee: The Johns Hopkins University, Baltimore, Md.

[21] Appl. No.: 09/267,448

[22] Filed: Mar. 12, 1999

Related U.S. Application Data

[62] Division of application No. 08/761,910, Dec. 9, 1996, Pat. No. 5,881,443.

[51] Int. Cl.[7] ............... B23D 11/02; A61F 2/28; A61F 2/30
[52] U.S. Cl. ............... 29/446; 29/33 R; 29/423; 29/515; 155/309.6; 264/259; 264/403; 425/111; 425/406; 623/16; 623/901
[58] Field of Search ............... 156/172, 309.6, 156/308.2; 623/16, 901; 425/89, 111, 117, 406; 264/16, 259, 403; 29/423, 447, 446, 515, 33 R, 460, 602.1

[56] References Cited

U.S. PATENT DOCUMENTS

| | | | |
|---|---|---|---|
| 3,761,557 | 9/1973 | Werner | 29/460 |
| 4,471,209 | 9/1984 | Hollander | 29/33 R |
| 4,943,794 | 7/1990 | Suzuki et al. | 29/602.1 X |
| 5,407,514 | 4/1995 | Butsell | 156/308.2 X |

*Primary Examiner*—William Briggs
*Attorney, Agent, or Firm*—Francis A. Cooch

[57] ABSTRACT

Apparatus and methods for partially embedding a biocompatible material, such as a titanium coil, in the surface of a polymer bone implant to provide a porous coating for bone cells to grow through thereby promoting long term stabilization of the implant. In one embodiment, the coil is wrapped around the implant and placed in a manifold where rollers biased by springs press against the coil. The coil-implant is rotated and heated by a hot gas stream, the rollers-springs pushing the coil into the surface of the implant. In a second embodiment, the coil is compressed and placed onto a needle wire which is placed against the surface of the implant. The point of contact is heated and the implant is rotated with the needle wire creating a channel in the softened polymer and feeding the coil, which is simultaneously stretched, therein. The needle wire then pulls the polymer over a portion of the coil as it passes. In a third embodiment, the coil is wrapped around the implant with an optional titanium foil then wrapped around the coil-implant. A ceramic clamp comprising at least two ceramic parts is placed around the foil(if used)-coil-implant and held in place by a nonconductive, elastic material. The coil-implant is then inductively heated with the coil being pushed into the softened surface of the implant by the pressure applied by the ceramic parts being compressed together by the elastic material. Alternatively, the titanium coil may be wrapped around the implant in sufficient tension that it will embed itself when inductively heated, without using the ceramic clamp and elastic material to apply pressure.

4 Claims, 9 Drawing Sheets

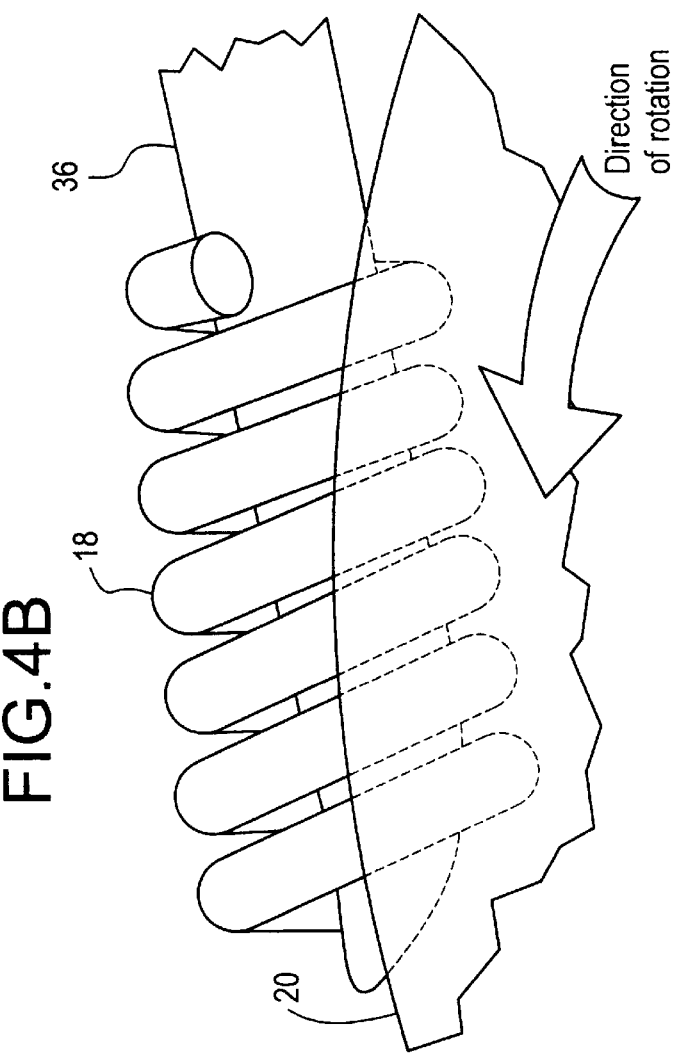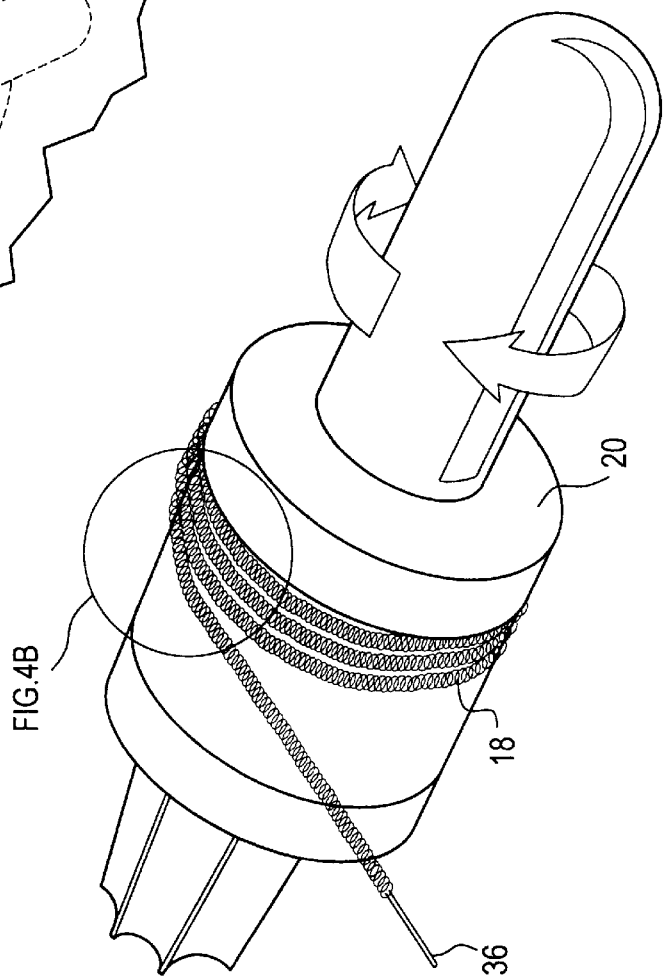

APPARATUS AND METHODS FOR EMBEDDING A BIOCOMPATIBLE MATERIAL IN A POLYMER BONE IMPLANT

CROSS-REFERENCE TO RELATED APPLICATION

This is a divisional of prior application Ser. No. 08/761,910, filed Dec. 9, 1996 U.S. Pat. No. 5,881,443.

STATEMENT OF GOVERNMENTAL INTEREST

This invention was made with Government support under Contract No. N00039-95-C-0001 awarded by the Department of the Navy. The Government has certain rights in the invention.

BACKGROUND OF THE INVENTION

The invention relates to orthopedic (bone) implants which are used to replace a missing or diseased portion of bone and, more specifically, to apparatus and methods for manufacturing such implants. Several conditions can lead to the loss of bone including trauma, arthritic diseases, tumors, musculoskeletal defects, and the replacement of a failed implant.

An intramedullary implant is generally used in long bones (i.e., the femur and humerus), and is inserted into the medullary canal, which runs through the diaphysis (shaft) of the bone and is filled with bone marrow. A long bone implant is one of two different types of intramedullary implants, the other being categorized as joint replacements. The joint replacement implants (i.e., a hip or knee implant) have a much more complicated geometry, than the rod-like, long bone replacement. Both types of implants have shown similar modes of failure in clinical studies.

The intramedullary implants being used today are generally fabricated from metal, using an alloy of either titanium (Ti) or cobalt chrome (Co—Cr). The joint replacement implants are primarily made with a Co—Cr alloy containing molybdenum (Mo), which is added to improve the wear resistance properties of the material, an important consideration when the implant is used to replace articulating surfaces.

Long bone replacement implants are most commonly fabricated from Ti, either in its commercially pure state or as an alloy with aluminum and vanadium. These materials have been experimentally and clinically proven to be biocompatible. It is not completely understood biochemically, but the bone tissue grows and attaches to the surface of Ti more readily than to other materials. This property allows Ti to aid in the fixation of the implant to bone, an extremely important factor directly affecting the implant's duration of success.

It is also important for implant success that the implant remain stationary so the bone tissue can begin to grow around it. Initial stabilization is achieved through the use of bone cement applied during surgery, which acts as a filler between the bone and the implant. The interfacial space is filled with cement to stabilize the implant and inhibit motion. The bone cement material is a thermoset particulate composite polymer called polymethylmethacrylate (PMMA).

Long term stabilization of the implant in bone is achieved by having a porous coating on the surface of the implant. The porous coating is either added or molded onto the surface of the implant. Ti or hydroxyapatite (HA) are two materials with good biocompatibility and/or biostimulating factors commonly used to create this porous coating. Ti is sintered onto the surface of the metal (e.g., Ti) implant in either a mesh of crimped wire or a random array of particulates. The HA is applied to the surface of the implant using plasma spraying techniques.

The porous coating must have large enough pores to allow the bone cells to travel through and create a strong interlocking fixation by reconnecting with adjacent bone tissue throughout the mesh. This method of fixation relies on the connection of the bone tissue to hold the implant in place. If the bone tissue does not grow fast or is not strong enough, the implant is not completely stabilized and micromotion can occur.

Problems with current implant designs originate from the difference in mechanical properties between the materials used in the implant system and the bone itself. The Ti alloy has an elastic modulus equal to 110.3 GPa ($16.0 \times 10^6$ psi), and the Co—Cr alloy has an elastic modulus equal to 210.3 GPa ($30.5 \times 10^6$ psi). In comparison to the modulus of cortical bone, equal to about 13.8 GPa ($2.0 \times 10^6$ psi), these metallic implants are a minimum of eight times stiffer. This large gradient causes stress shielding across the implant-bone interface, where the implant supports and absorbs most of the load and leaves the bone virtually inactive and unstressed.

As stated in Wolff's law, bone needs to be cyclically stressed to survive and remain strong enough to support the body. The shielded, unstressed bone around a metal implant begins to resorb and cavities form between the implant and the bone. The cavities weaken the fixation and allow micromotion of the implant in the bone, eventually producing local wear debris. Microscopic foreign body wear debris in the surrounding tissue will trigger the body's defense mechanism and cause infectious reactions. Loosening of the implant is irreversible without intervention and ultimately leads to a revision operation. A patient can only undergo two or three additional procedures before the bone becomes too weak and osteoporotic to support another replacement and is considered non-functional.

A polymer bone implant minimizes, if not eliminates, the stress shielding effect created by a metal implant, thus, leading to a longer implant lifetime in the body. The polymer bone implant can comprise a thermoplastic polymer with an elastic modulus approximating the modulus of bone or a composite comprising a thermoplastic polymer and a reinforcing material, the composite also having an elastic modulus approximating the elastic modulus of bone.

The final step in the manufacture of the polymer bone implant is the application or formation of the porous coating on the surface of the implant to create the porous environment for bone ingrowth, as discussed above. The coating can comprise hydroxyapatite applied to the surface, a roughness formed on the surface, or a biocompatible material such as titanium. The use of this latter type of porous coating requires new apparatus and methods for embedding the biocompatible material in the polymer bone implant surface.

SUMMARY OF THE INVENTION

In a first embodiment, a biocompatible material, such as a titanium coil, is initially wrapped around a polymer bone implant, as described and claimed in U.S. patent application Ser. No. 08/742,733, filed Nov. 1, 1996, which is incorporated herein by reference. The combined coil-implant is then placed in a manifold comprising a hot gas input port and a plurality of output openings. The coil-implant when in the manifold has at least one and preferably four rollers pressing against the coil; the rollers are forced against the coil through the use of a biasing means, such as a spring.

In operation, the implant is rotated while a hot gas is fed through the openings in the manifold to heat the coil-implant. When the titanium coil becomes hot and the polymer of the implant softens, the rollers and springs push the titanium coil into the surface of the implant. Stopping means are located in the rollers-springs to prevent the titanium coil from being pushed more than ⅓ to ½ of its diameter into the surface of the implant.

In a second embodiment, a coil of a biocompatible material, preferably titanium, is compressed to the point where almost no space remains between individual coils. The length of the coil is determined so one continuous piece will provide the coverage desired over the surface of the implant. The compressed coil is then slid onto a needle wire; the tip of the needle wire is placed against the surface of the implant; and the point of contact is spot heated to soften the implant's surface. Thereafter, the implant is rotated with the simultaneous stretching and feeding of the coil to the surface of the implant, the tip of the needle wire pushing away the softened surface to create a channel for the coil. The coil is laid in the channel and the tip of the needle wire as it passes pulls the softened surface of the implant over the bottom of the coil, thereby partially embedding the coil. As in the first embodiment, the coil should be embedded no more than from ⅓ to ½ of its diameter.

In the third embodiment, induction heating and a ceramic clamp are used to partially embed a biocompatible material such as a titanium coil in the surface of the polymer bone implant. As in the first embodiment, the titanium coil is initially wrapped around the implant. An optional interface means, e.g., a titanium foil slip sheet, may be used to cover the coil-implant. The ceramic clamp comprising at least two ceramic parts is then placed around the interface means, if used, and a nonconductive, elastic material, e.g., rubber or compression bands, is wrapped around the ceramic parts to hold them in place and apply pressure. The entire apparatus is then placed into an induction coil.

The titanium is inductively heated and, as a result, softens the implant with which it is in contact. The elastic material compresses the ceramic clamp parts together pushing the titanium coil into the softened surface of the implant. The interior diameter of the ceramic clamp is designed such that when it is fully compressed, i.e., the ceramic parts are in contact with each other, pressure can no longer be applied to the titanium coil, which at that point is then embedded from ⅓ to ½ of its diameter into the surface of the implant. Alternatively, the titanium coil may be wrapped around the implant in sufficient tension that it will embed itself when inductively heated, without using the ceramic clamp and elastic material to apply pressure.

BRIEF DESCRIPTION OF THE DRAWINGS

FIG. 4 consisting of FIGS. 4*a* and 4*b*, illustrates a method of the second embodiment of the invention wherein a titanium coil is embedded in the surface of a polymer bone implant as it is wrapped around the implant.

DETAILED DESCRIPTION OF THE INVENTION

The first step in producing a polymer bone implant, as discussed in U.S. patent application Ser. No. 08/742,733, filed Nov. 1, 1996, which is incorporated herein by reference, was to develop a material that has similar bulk mechanical properties to those of bone. A number of polymers have such properties including some polymers that may be stiff enough to use as an implant without the need for reinforcing fibers, e.g., Poly-X™ Self-Reinforced Polymers manufactured by Maxdem Inc. of San Dimas, Calif. A key aspect is the use of a material as an implant that has an elastic modulus approximating the elastic modulus of bone.

For a composite implant, a high temperature thermoplastic polymer, polyetheretherketone (PEEK), was chosen as the resin, or matrix, material for its relatively comparable strength, high toughness and previously recorded biocompatibility with human tissue cells. E-glass fibers were selected as the reinforcing material for their strength.

Although carbon fibers can be used in PEEK, glass fibers were chosen because the material was more cost effective, and the injection molding of the preforms was easier because the glass fibers are less abrasive than carbon. Most importantly, the glass fibers are transparent to radiation therapy and will not create shadows or interfere with post-operative treatment.

While the stress that the composite implant bears is much lower than that for the metallic implant, the stress in the cement and bone layers are higher for the composite implant than for the Ti. This is a direct result of matching the elastic modulus of the composite to that of bone. The composite implant is not bearing as much load as the metallic implant, allowing the bone to absorb more of the applied load. Therefore, the cortical bone layer bears more load when using the composite implant, theoretically confirming that an implant with properties closer to that of bone leads to the elimination of the stress shielding effect evident with higher modulus metallic implants.

Figure 1:
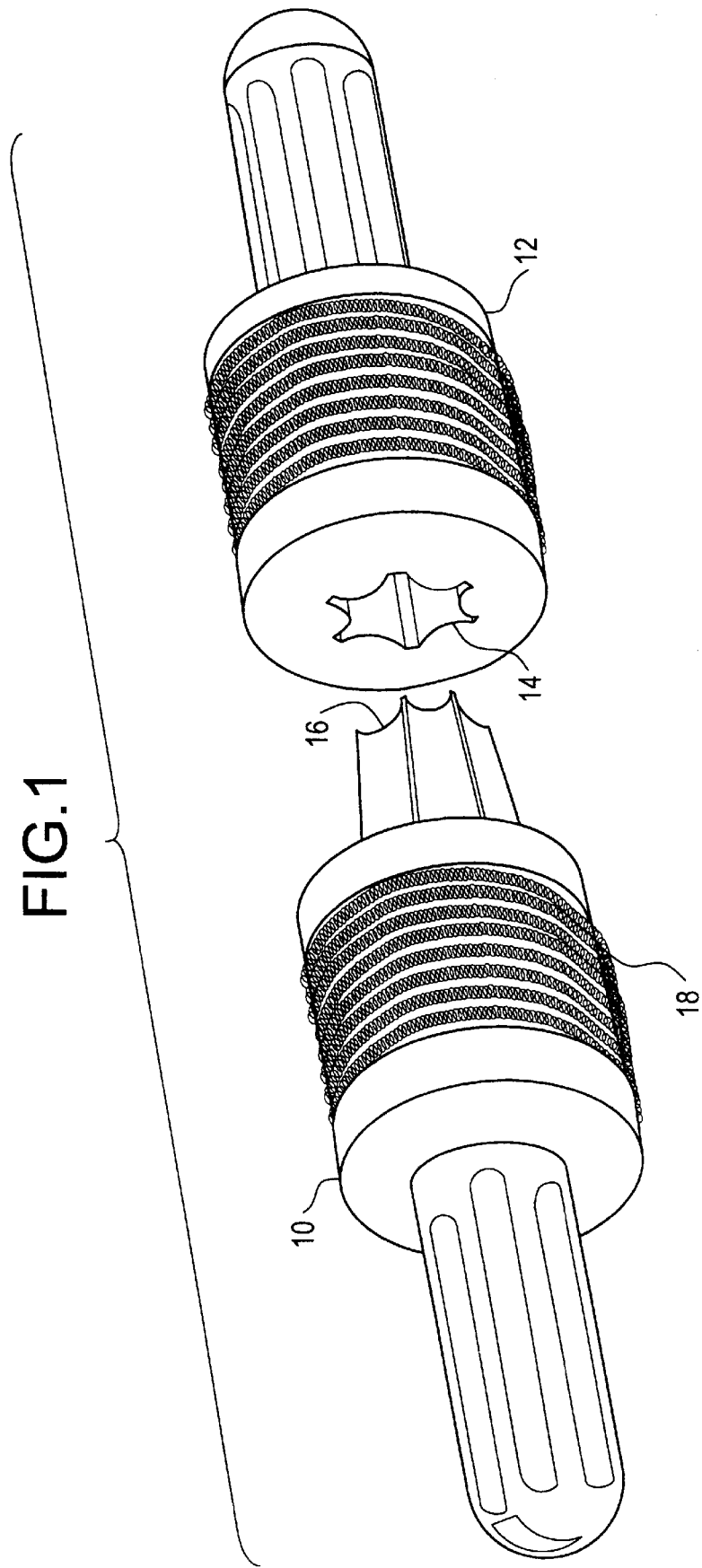
FIG. 1 illustrates a polymer bone implant.

As shown in FIG. 1, an implant comprises first and second pieces 10, 12, each with a tip or end that fits into the intramedullary canal and extends from a wider portion that has the porous coating to support the growth of extracortical bone. Each tip is inserted into the medullary cavity of either end of the fractured bone at the diseased or damaged site deep enough to assure anchorage into healthy bone. The second piece has a cavity 14 for receiving a protruding member 16 on the first piece. The two pieces which are complementarily tapered for ease of alignment and assembly are joined by being tapped together and locked by the tapered press fit.

The intramedullary implant is also designed with a means for resisting rotation between the first and second pieces. In one embodiment this comprises a six-fluted interlock to insure that the implant is rotationally stable. Flutes were chosen to minimize stress concentration while maximizing interlock or fixation but any keyed or indexed means to prevent rotation, such as notches and recesses, are acceptable. In addition to using an adhesive to seal this connection, the mating flutes apply a positive lock during torsion.

The design of a six-fluted mating interlock is alterable in consideration of the surgical procedure for implanting these devices. The addition of more flutes would retain the strength and resistance to torsional forces, while decreasing the angle between each mating flute. This decrease in angle would make it much easier to match the two halves when securing them together during surgery, where time may be a major concern.

The interlocking flutes are molded onto/into the ends of the preforms, and are designed to have a friction lock when tapped together, making the sizing and accuracy of the molding very critical. The flutes on the tips (the ends that are inserted into the medullary cavity of bone) provide more surface area for the bone cement to fill and hold the implant in place.

The final step in making the implant is to embed a biocompatible material, such as a titanium coil 18 (FIG. 1), into the surface of the body of the implant by, for example, wrapping the coil around the implant and pressing the coil into the polymer after or during an application of heat. Titanium is used for its biocompatibility. The critical design aspect of this surface, aside from achieving a strong attachment of the titanium to the composite, is its porosity. In order to allow the necessary bone cells to fit through the pores and create the desired mechanical interlock, the pores, i.e., the interstices between the exposed (nonembedded) portions of the titanium wire coil, should be in the range of 150–200 $\mu$m which may require that the wire coil be inter-meshed, i.e., overlapped, to achieve.

The titanium coil can be embedded into the polymer via one of several methods, all of which should be done in a vacuum or inert gas atmosphere: 1) the coil is heated via electrical resistance while being pressed into the polymer; 2) the coil is preheated in an oven and then placed around the polymer while being pressed into place; 3) the coil and polymer surface are both heated by a focused hot gas stream while the coil is pressed into the polymer; 4) the coil and the polymer are both heated at the intersection point by a focused infrared beam while the coil is wrapped around the polymeric implant and embedded; and 5) the coil is heated by induction in a high frequency RF field while being pressed into the polymeric surface. In each case the coil should only be embedded from ⅓ to ½ of its diameter in the surface of the polymer bone implant when the process is completed. Also, the mechanism for embedding the coil should not interfere with the heating method. It is the last three above-described methods to which the inventions described and claimed herein are directed.

Figure 2:
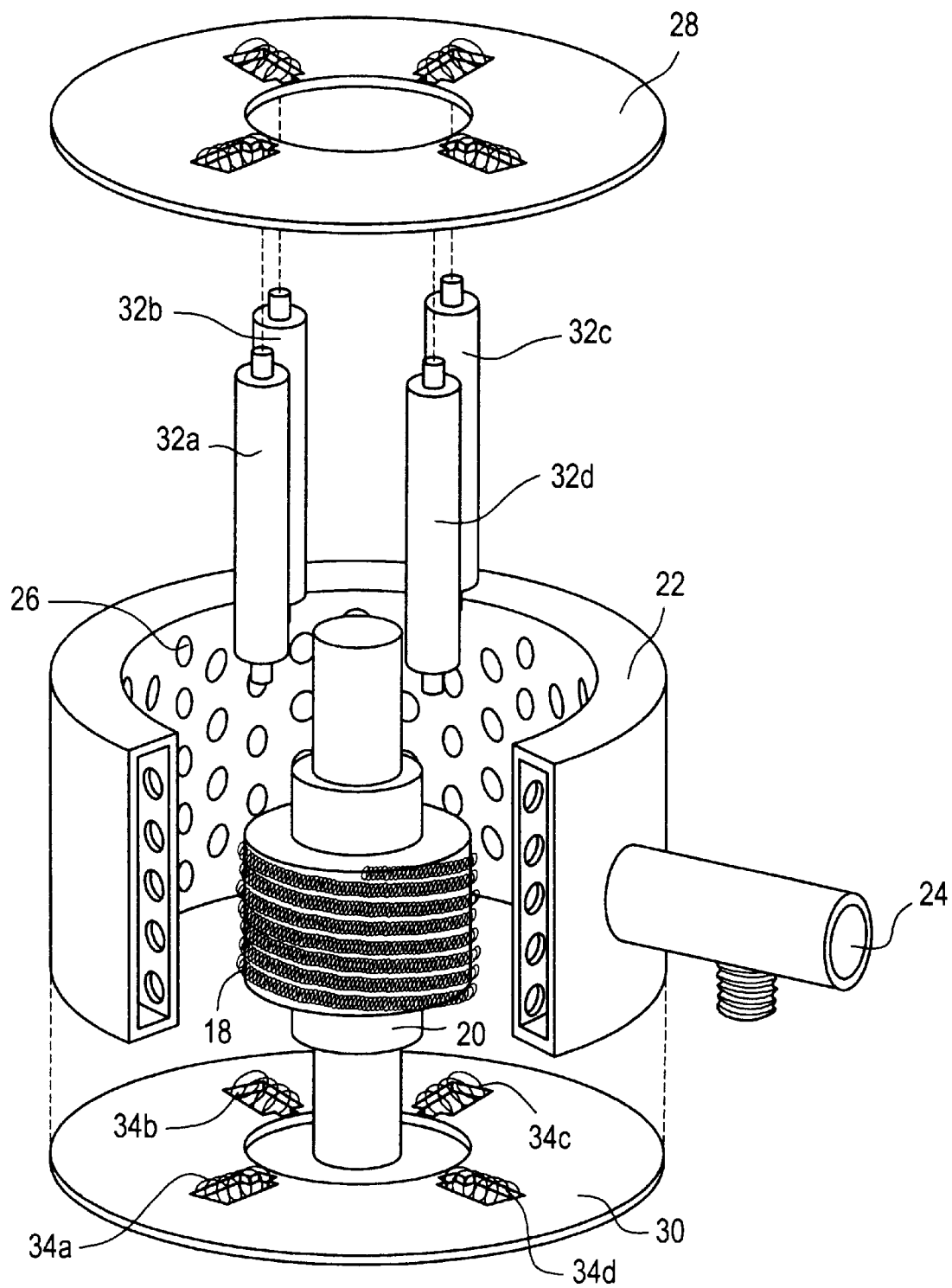
FIG. 2 illustrates an exploded view of an apparatus of a first embodiment of the invention for embedding a titanium coil into the surface of a polymer bone implant.

In a first embodiment, illustrated in FIG. 2, a biocompatible material, such as a titanium coil 18, is initially wrapped around the polymer bone implant 20 and then the combined coil-implant is placed in a manifold 22 and held there with a rod (not shown) that fits on the protruding tip of the implant. The manifold comprises a hot gas input port 24 and a plurality of output openings 26. End plates 28, 30 hold at least one and preferably four rollers 32*a*, 32*b*, 32*c* and 32*d* and biasing means such as springs 34*a*, 34*b*, 34*c* and 34*d* for forcing the rollers against the coil-implant.

Figure 3:
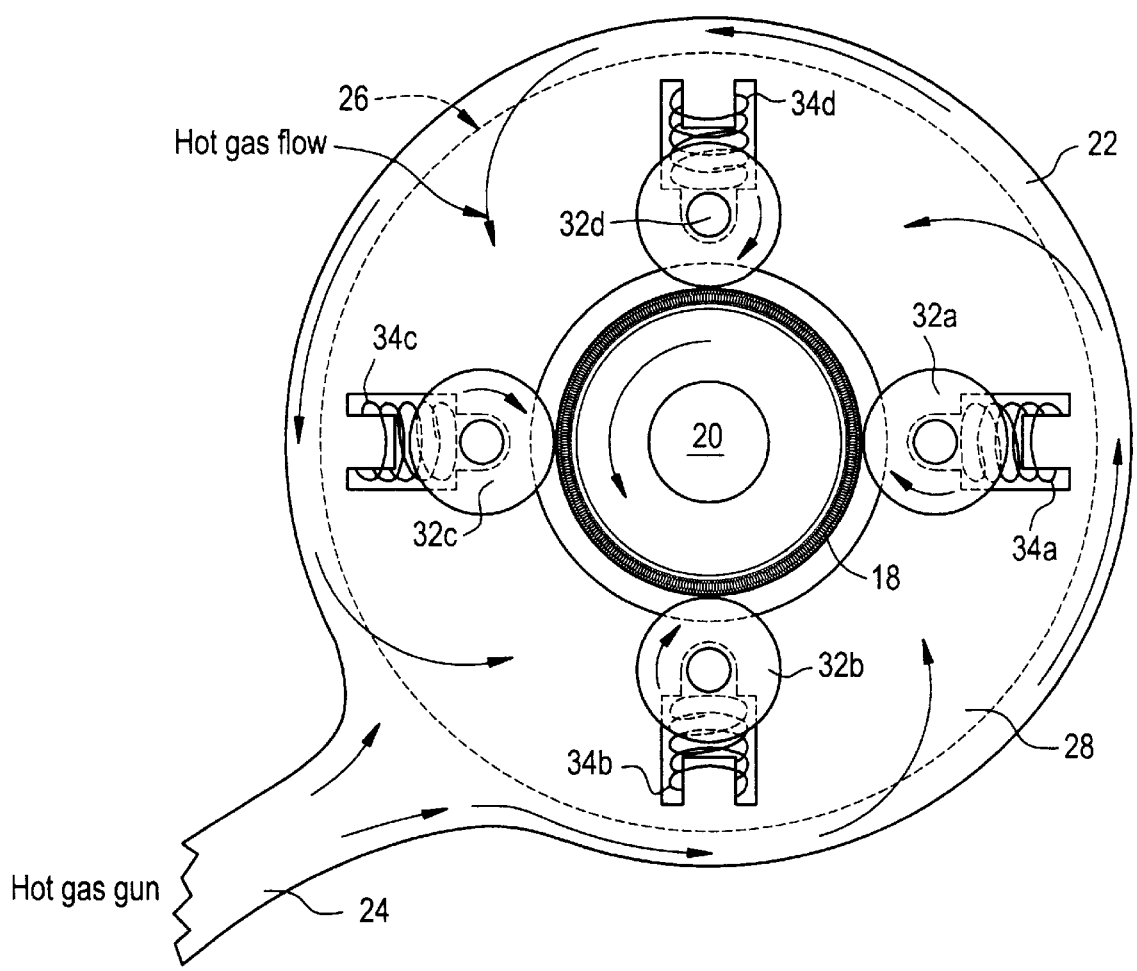
FIG. 3 illustrates an end view of the apparatus of FIG. 2 while in operation.

In operation, the coil-implant is inserted inside the manifold and, as shown in FIG. 3, pushes the rollers out compressing the springs. The coil-implant is then rotated while hot gas is fed through the output openings in the manifold to heat the coil-implant. When the titanium coil becomes hot and the polymer of the implant softens, particularly where the implant is contacted by the coil, the titanium coil will embed into the surface of the implant, pushed in by the rollers and the expanding force of the springs. The rollers-springs contain stopping means, i.e., the retractive force of the springs pushes the rollers until the ends of each roller hit notches in the end plates. At this point, the titanium coil will have been pushed from ⅓ to ½ of its diameter into the surface of the implant. The continuous rotation of the implant against the rollers provides a uniform pressure on the entire surface (the entire coil wrapped surface fits in the manifold at one time) and creates a uniform imbedding of the titanium coil.

In a second embodiment, shown in FIGS. 4*a* and 4*b*, a coil of a biocompatible material, preferably titanium 18, is compressed to the point where almost no space remains between individual coils. The length of the coil is determined so one continuous piece will provide the coverage desired over the surface of the implant. The compressed coil is then slid onto a needle wire 36 and the tip of the needle wire is placed against the surface of the implant 20.

The tip of the needle wire is designed to act as a shovel and a guide for the coil. The machined tip rests along a tangent line to the surface of the implant and matches its curvature.

A focused heating source is aimed at the location where the needle wire's tip contacts the surface of the implant. The implant at the point of contact is then spot heated to soften, but not necessarily turn molten, the implant's surface.

Thereafter, the implant is continuously rotated at a speed to match that of the wire feed. The motion turns the implant away from the point where the wire is hitting the implant surface (i.e., the motion will help in pulling the coil off the wire, which remains stationary and laying on the surface). As the implant rotates, the softened surface of the implant is pushed away by the tip of the needle wire, creating a channel.

In one continuous motion, the coil is stretched (opened), fed to the surface of the implant and laid in the channel. This is a controlled action and is consistent for the entire length of coil. The amount the coil is opened is predetermined and dependent on the desired porosity of the resultant porous coating.

The tip pulls the softened surface material over the bottom of the coil. The coil is thereby partially embedded and completely secure in the surface. As in the first embodiment, the coil should be embedded no more than from ⅓ to ½ of its diameter.

Figure 5:
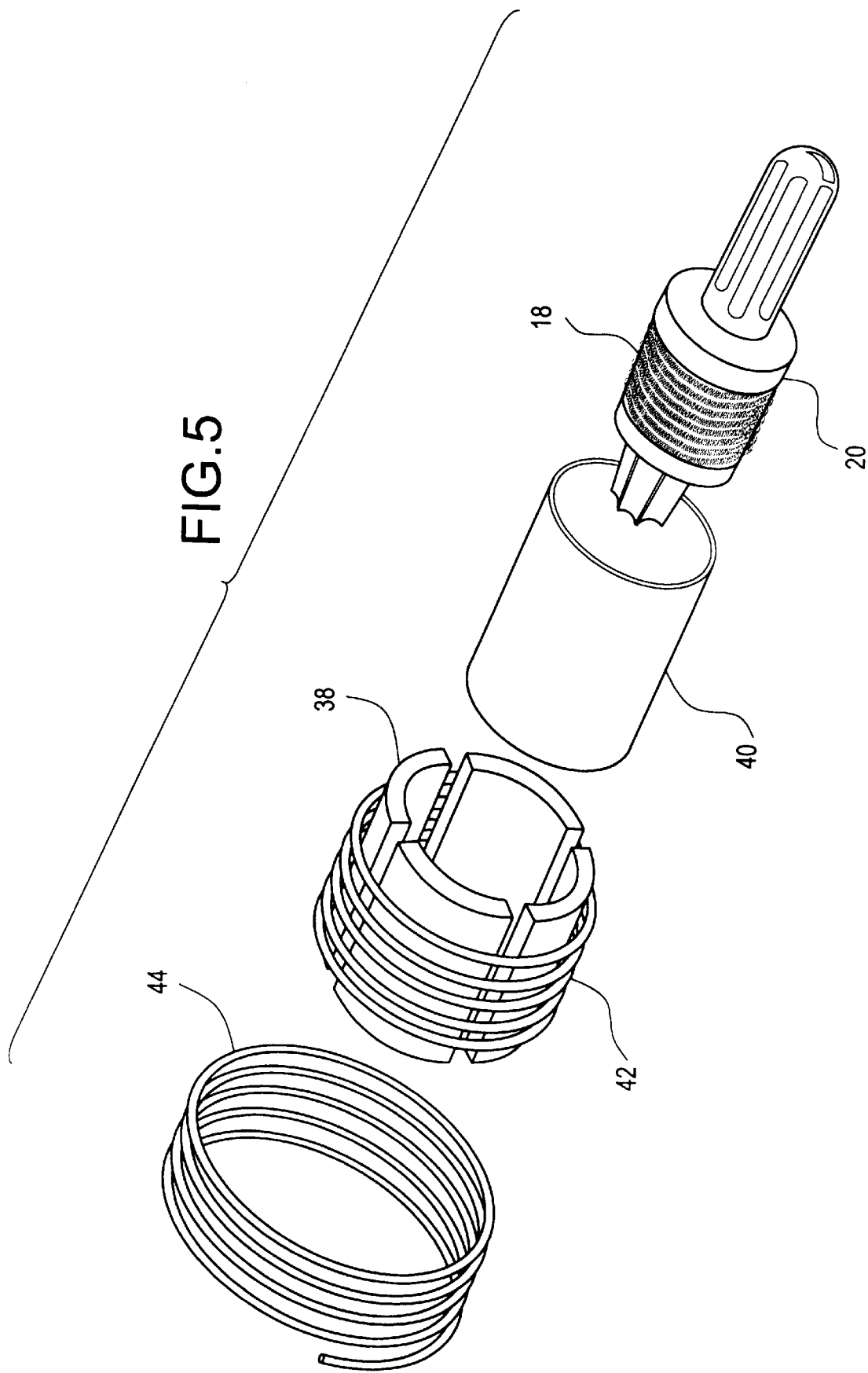
FIG. 5 illustrates apparatus of the third embodiment of the invention utilizing a ceramic clamp and induction heating to embed a titanium coil into the surface of a polymer bone implant.

In the third embodiment, shown in FIG. 5, induction heating and a ceramic clamp 38 are used to partially embed a biocompatible material such as a titanium coil 18 in the surface of the polymer bone implant 20. As in the first embodiment, the coil is initially wrapped around the implant, the coil sitting on top of the implant surface. An optional interface means, e.g., a titanium foil slip sheet in the form of a sleeve, may be used to cover the coil-implant to ensure that the coil does not interfere with the movement of the ceramic clamp, although the titanium foil slip sheet may prevent a portion of the coil from becoming properly heated.

The ceramic clamp comprising at least two and preferably four ceramic parts is then placed around the interface means, or, if no interface means is used, the ceramic clamp may be placed directly on the coil, and a nonconductive, elastic material, e.g., rubber or other compression bands 42, initially in tension, is wrapped around the ceramic parts to hold them in place and apply pressure. The ceramic clamp is designed to have an inner diameter, when it is fully closed/compressed, i.e., the ceramic parts are in contact with each other, equal to the outer diameter of the implant plus the titanium coil (embedded from ⅓ to ½ of its diameter) and, if used, the thickness of the titanium foil slip sheet. At that point, pressure can no longer be applied to the titanium coil which is then embedded from ⅓ to ½ of its diameter into the surface of the implant.

The entire clamp-titanium foil(if used)-coil-implant system apparatus is then placed into an induction coil 44. The titanium is inductively heated and, as a result, heats and softens the implant surface with which it is in contact. The ceramic clamp will be virtually unaffected due to its extremely high melting point and nonconductivity. The resistance from the implant to the pressure from the elastic material will decrease as it softens, allowing the ceramic clamp to close (via the elastic material compressing the ceramic parts) and the titanium coil to be pushed into the surface of the implant.

An alternative to the use of a ceramic clamp is to use no clamp at all. Instead, the titanium coil is wrapped sufficiently tightly around the implant as to leave the coil in tension. Then when the coil is inductively heated and softens the surface of the implant with which it is in contact, the tension in the coil will pull it into the implant's surface causing it to embed.

Figure 6A:
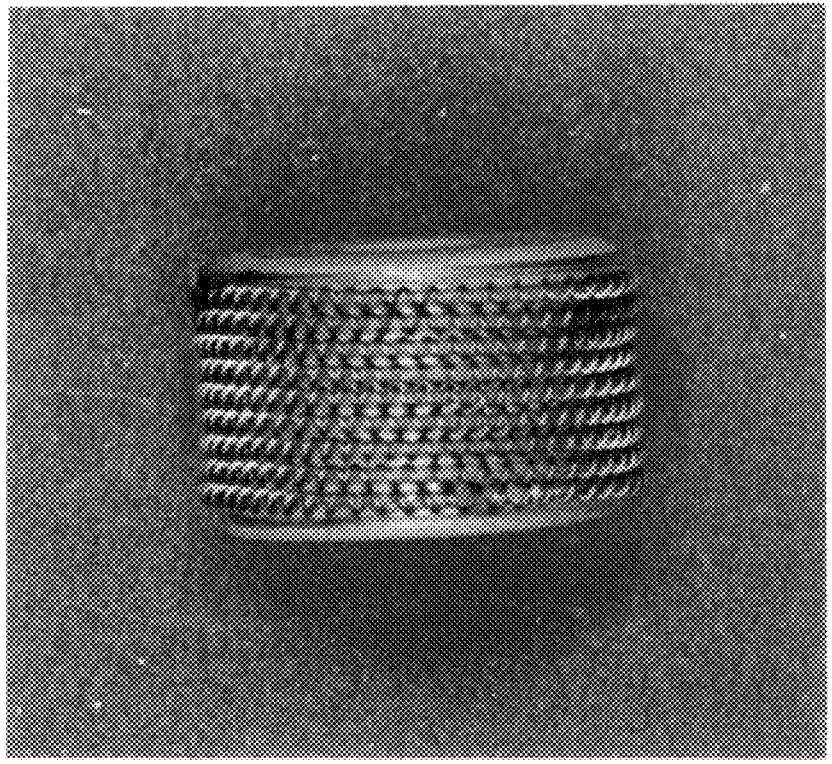
FIG. 6 consisting of FIGS. 6*a* and 6*b*, shows, respectively, the winding of the Ti coil around [a section of] the implant; and a magnified picture of the embedded Ti in the surface of the PEEK.
Figure 6B:
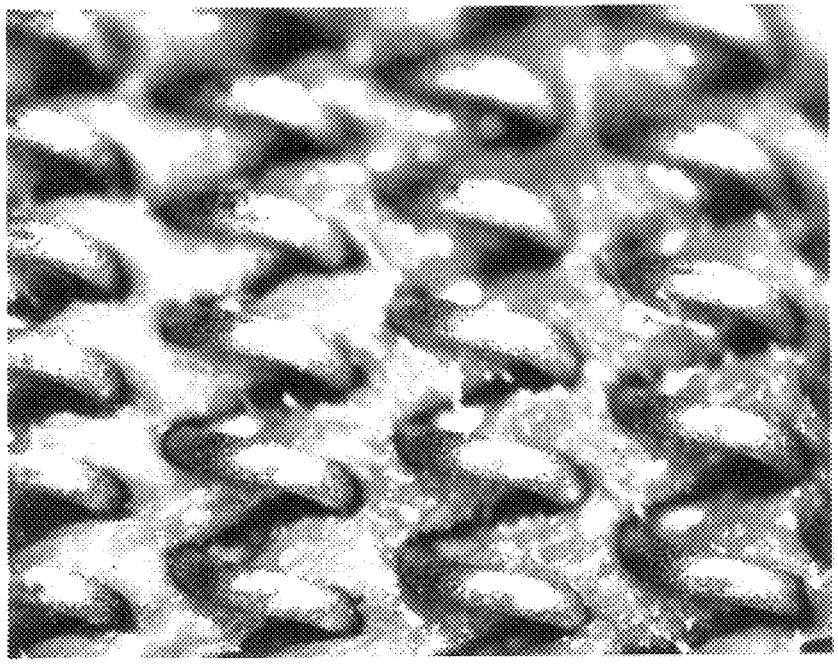

The result of using any one of the embodiments discussed above is a process that leaves the titanium coil embedded into the surface of the implant approximately halfway, as shown in the photographs in FIGS. 6a and 6b. Push out tests were performed to prove the titanium coil was securely embedded and mechanically locked into the surface of the implant. For each test, a section of the implant was set in an epoxy, using a 33:100 ratio of EPON Curing Agent V-40 to EPON Resin 826. The epoxy represented bone tissue surrounding the implant, creating a mechanical interlock through and around the titanium coil. The tests were done on an Instron Machine performing general compression of a cylinder.

Figure 7:
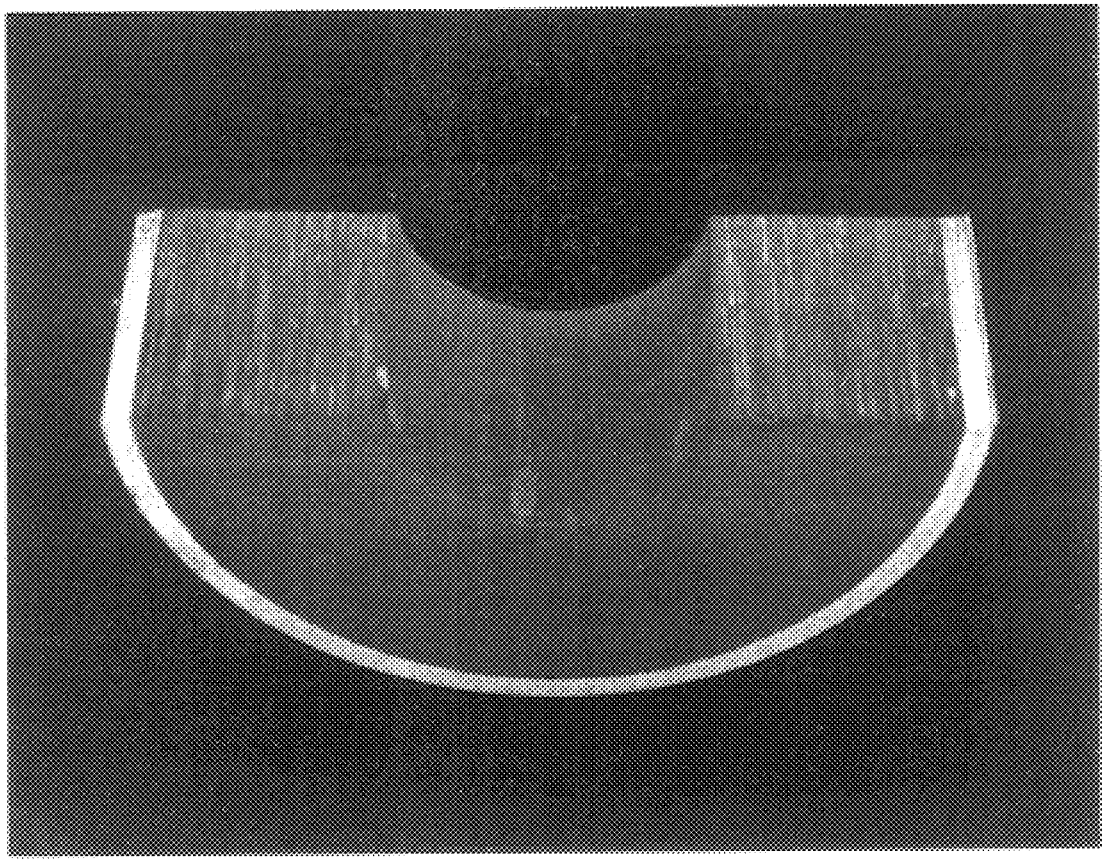
FIG. 7 illustrates a push-out test cross-section of epoxy (magnified 2x), representing bone tissue, that surrounded a PEEK implant that did not have a Ti wire coil embedded in the implant surface.

In order to prove that the results of the push-out tests represent the forces at the interface of the coil and the epoxy, instead of the implant surface and the epoxy, an initial test was done using a section of the implant without any coil embedded in the surface. The results showed that there was no bonding of the epoxy to the implant surface. The implant was smoothly pushed out with a maximum load of 540 lb, creating a shear stress of 419 psi. FIG. 7 is a cross-sectional picture of the epoxy that surrounded the part. It is obvious that there was no shearing or failure of the epoxy, which would have resulted if it bonded with the implant surface.

Tests were then done using sections of the implant with the coil embedded in the surface. Three tests were done with a low rate of displacement, applied at a constant 0.05 in/min. The maximum recorded push out load was an average of 3386 lbs, with an average maximum shear stress of 2269 psi. Test 4 was done with a higher rate of displacement, applied at a constant 10 in/min. The maximum force approximately doubled compared to the slower tests.

Figure 8:
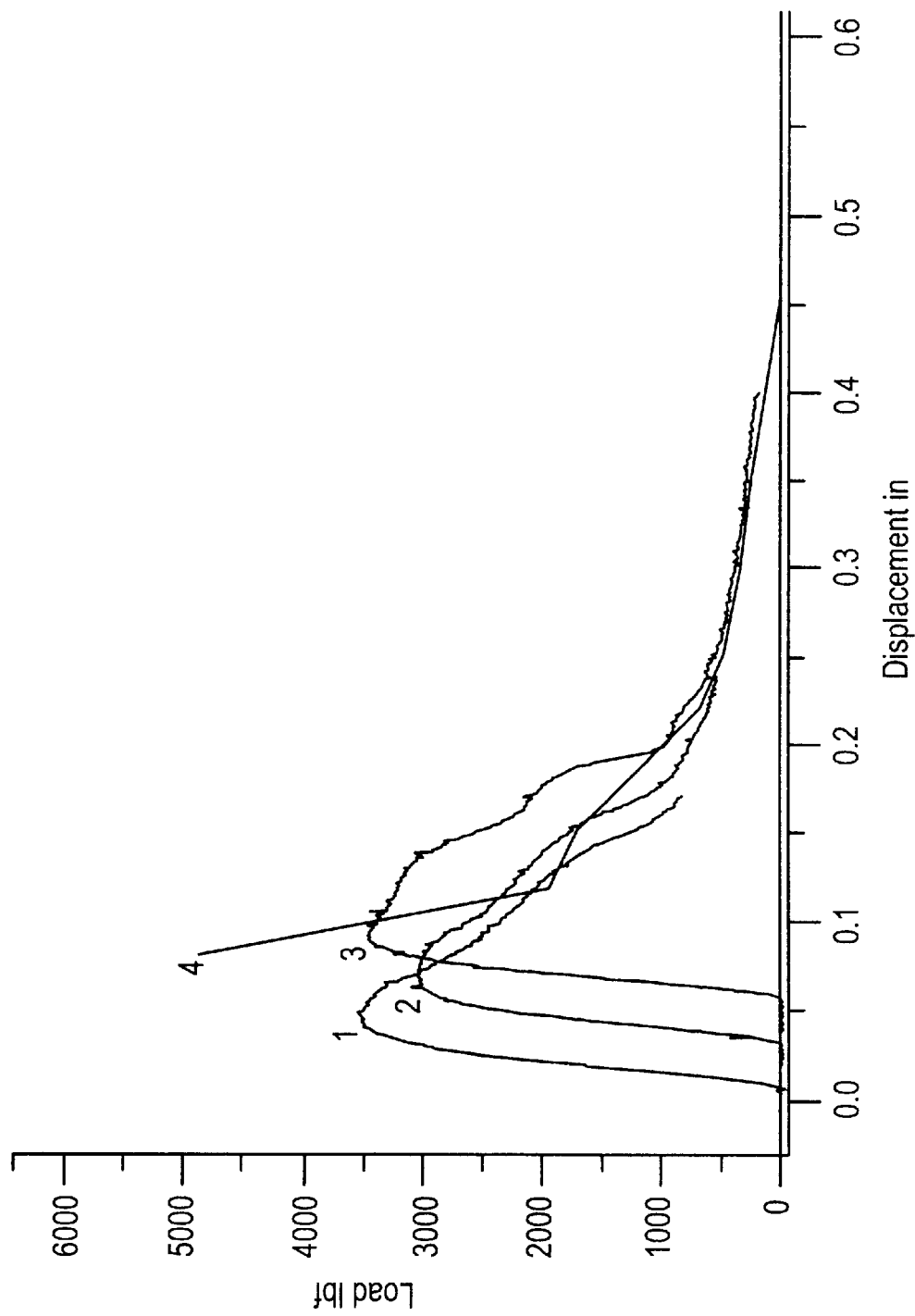
FIG. 8 is a plot of load v. displacement for four push-out tests for sections of epoxy, representing bone tissue, surrounding a PEEK implant having a Ti wire coil embedded in the implant surface.
Figure 9:
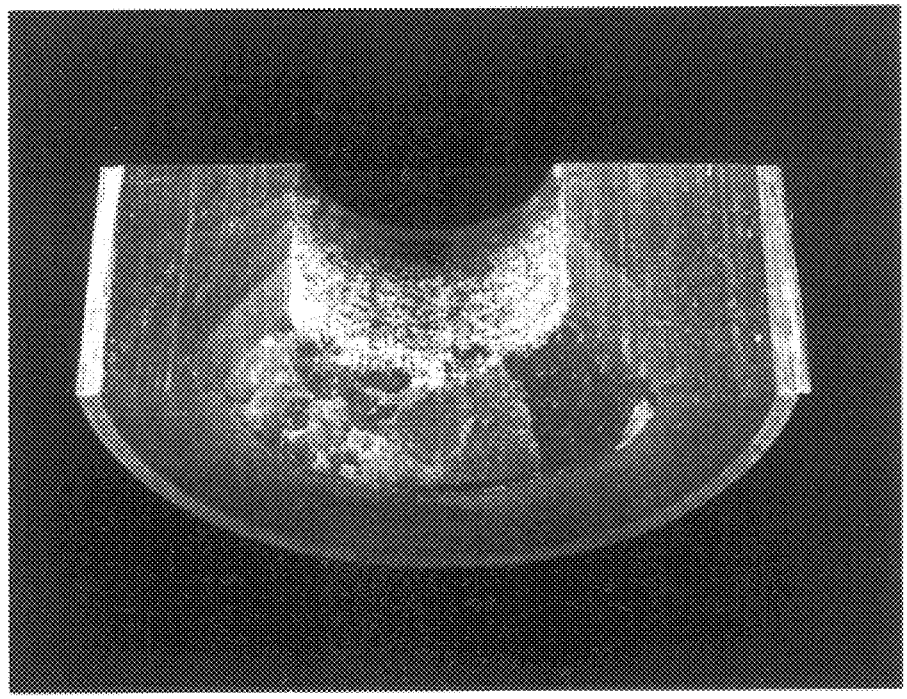
FIG. 9 illustrates a push-out cross-section of the epoxy (magnified 2x), representing bone tissue, that surrounded the PEEK implant with Ti wire coil embedded therein.
Figure 10:
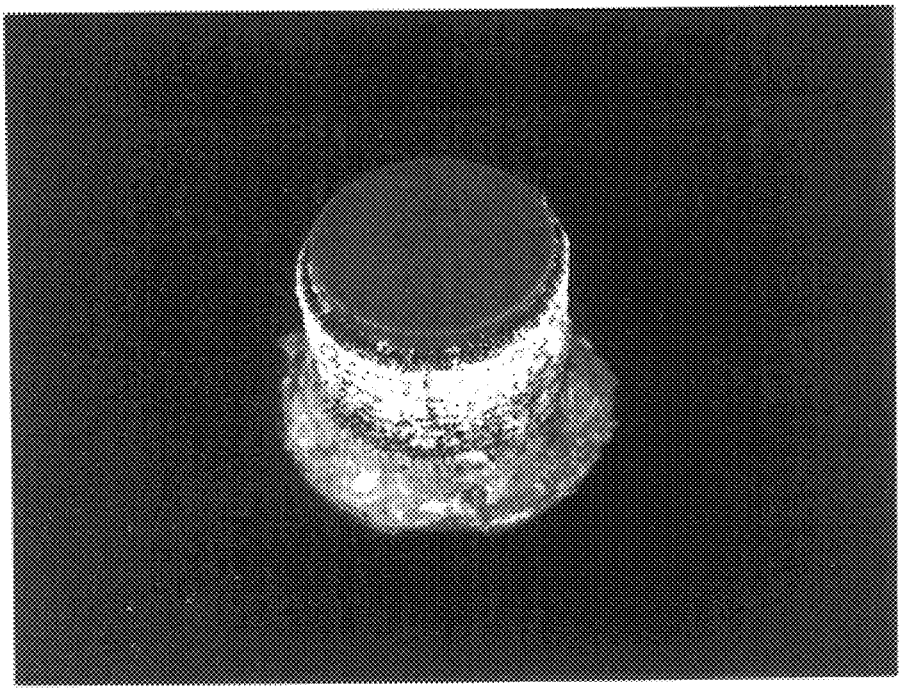
FIG. 10 illustrates the PEEK implant with embedded Ti wire coil (magnified 2x) after being pushed completely through the epoxy.

The load vs. displacement curves for all tests are shown in FIG. 8. The consistency is obvious with tests 1–3 and a steeper slope is shown for test 4 (this maximum force was not recorded quickly enough and was therefore estimated from the ultimate shear stress of the epoxy, since the epoxy completely failed). FIG. 9 is a cross-sectional picture of the epoxy that surrounded the part. The titanium sheared out of the epoxy and remained completely anchored in the implant surface, eventually fracturing the epoxy. The mechanical interlock of the epoxy in the coil pulled the epoxy with it as it was pushed through. FIG. 10 shows the part after being pushed completely through the epoxy. The amount of epoxy that remained attached to the coil proves that the mechanical interlock of the material through the porous surface is extremely strong.

The push out tests confirm that the titanium coil is mechanically locked in the surface of the implant. Considering that the most damaging strain the implant/coil interface would experience when implanted in vivo is in shear, these tests have proven that the titanium coil is essentially permanent in the surface. The amount of epoxy remaining in the coil as it was pushed through shows that this type of porous surface is more than adequate at providing enough space for a material (i.e., the epoxy in the test and bone tissue in vivo) to grow throughout it and create a mechanical interlock. Test 4 (performed with a higher rate of displacement) simulates a worst case scenario of the force the implant might see if the repaired bone experiences a major impact.

Clinically, the use of an implant that has an elastic modulus approximating the elastic modulus of bone will have a great impact on the orthopedic industry. Long term advantages of this new technology include a decline in the amount of revision surgeries necessary, reducing the rise of health care costs. The new implant will have a longer fatigue life, which will better serve the younger patient population, with a lower probability of recurring pain and surgery for the patient.

We claim:

1. Apparatus for uniformly and partially embedding a titanium coil in the surface of a polymer bone implant, the coil being initially wrapped around the implant, the apparatus comprising:

a manifold surrounding the coil-implant, the manifold comprising a hot gas input port and a plurality of output openings;

a means for rotating the coil-implant;

a roller, the roller pressing against the coil as the coil implant is rotated;

a spring for forcing the roller against the coil and pushing the coil into the surface of the implant as the coil and implant are heated; and means for stopping the roller from pressing further against the coil once the coil is partially embedded from ⅓ to ½ of its diameter in the surface of the implant.

2. A method for partially embedding a coil of a biocompatible material in the surface of a polymer bone implant, the method comprising the steps of:

compressing a length of the coil;

sliding the compressed coil onto a needle wire;

placing the tip of the needle wire against the surface of the implant;

heating the surface of the implant where the tip of the needle wire contacts the surface of the implant, thereby softening the surface;

simultaneously rotating the implant and stretching and feeding the coil to the surface of the implant, the tip of the needle wire pushing away the softened surface of the implant thereby creating a channel for the coil, the tip of needle wire as it passes pulling the softened surface of the implant over the bottom of the coil, thereby partially embedding the coil.

3. The method as recited in claim 2, wherein the coil is embedded in the surface of the implant between ⅓ and ½ of its diameter.

4. The method as recited in claim 3, wherein the biocompatible material is titanium.

* * * * *